US009645109B2

(12) United States Patent
Jin et al.

(10) Patent No.: US 9,645,109 B2
(45) Date of Patent: May 9, 2017

(54) SCANNING DROP SENSOR

(71) Applicants: California Institute of Technology, Pasadena, CA (US); LAWRENCE BERKELEY NATIONAL LABORATORY, Berkeley, CA (US)

(72) Inventors: Jian Jin, Berkeley, CA (US); Chengxiang Xiang, Costa Mesa, CA (US); John M. Gregoire, Sierra Madre, CA (US); Aniketa A. Shinde, Upland, CA (US); Dan W. Guevarra, Norwalk, CA (US); Ryan J. Jones, Pasadena, CA (US); Martin R. Marcin, Simi Valley, CA (US); Slobodan Mitrovic, Pasadena, CA (US)

(73) Assignees: California Institute of Technology, Pasadena, CA (US); Lawrence Berkeley National Laboratory, Berkeley, CA (US)

( * ) Notice: Subject to any disclaimer, the term of this patent is extended or adjusted under 35 U.S.C. 154(b) by 210 days.

(21) Appl. No.: 14/683,596

(22) Filed: Apr. 10, 2015

(65) Prior Publication Data
US 2015/0212036 A1 Jul. 30, 2015

Related U.S. Application Data

(63) Continuation-in-part of application No. 13/907,512, filed on May 31, 2013.
(Continued)

(51) Int. Cl.
G01N 27/403 (2006.01)
G01N 27/417 (2006.01)
G01N 27/416 (2006.01)

(52) U.S. Cl.
CPC ....... *G01N 27/4035* (2013.01); *G01N 27/416* (2013.01); *G01N 27/417* (2013.01)

(58) Field of Classification Search
CPC . G01N 27/416; G01N 27/417; G01N 27/4035
See application file for complete search history.

(56) References Cited

U.S. PATENT DOCUMENTS

| 4,179,349 A | 12/1979 | Park |
| 2008/0285099 A1 | 11/2008 | Knutson et al. |

(Continued)

FOREIGN PATENT DOCUMENTS

| WO | 2011091379 A1 | 7/2011 |
| WO | 2013181629 A1 | 12/2013 |

OTHER PUBLICATIONS

Lai et al. (J. Am. Chem. Soc., 2011, 133, 10744, in parent U.S. Appl. No. 13/907,512, Jul. 6, 2016, 4 pages).*
(Continued)

*Primary Examiner* — Matthew Martin
*Assistant Examiner* — Steven E Rosenwald
(74) *Attorney, Agent, or Firm* — Joseph R. Baker, Jr.; Gavrilovich, Dodd & Lindsey LLP

(57) ABSTRACT

Electrochemical or electrochemical and photochemical experiments are performed on a collection of samples by suspending a drop of electrolyte solution between an electrochemical experiment probe and one of the samples that serves as a test sample. During the electrochemical experiment, the electrolyte solution is added to the drop and an output solution is removed from the drop. The probe and collection of samples can be moved relative to one another so the probe can be scanned across the samples.

17 Claims, 4 Drawing Sheets

Related U.S. Application Data

(60) Provisional application No. 61/979,298, filed on Apr. 14, 2014, provisional application No. 61/654,198, filed on Jun. 1, 2012.

(56) References Cited

U.S. PATENT DOCUMENTS

2009/0316157 A1    12/2009  Saraf et al.
2011/0147213 A1     6/2011  Auerswald et al.
2013/0324424 A1*   12/2013  Jin .................... G01N 27/4035
                                                                     506/7

OTHER PUBLICATIONS

Laslau et al. (Adv. Funct. Mater. 2011, 21, 4607-4616, in parent U.S. Appl. No. 13/907,512, Jul. 6, 2016, 10 pages).*

Baharlou, Simin, International Preliminary Report on Patentability and Written Opinion, PCT/US2013/043766, The International Bureau of WIPO, Dec. 11, 2014.

Park, Jin Ho, International Search Report and Written Opinion, PCT/US2013/043766, Korean Intellectual Property Office, Sep. 2, 2013.

* cited by examiner

SCANNING DROP SENSOR

CROSS REFERENCE TO RELATED APPLICATIONS

This application claims the benefit of U.S. patent Ser. No. 13/907,512, filed May 31, 2013, which claims the benefit of U.S. Provisional Patent Application Ser. No. 61/654,198, filed on Jun. 1, 2012; this application also claims the benefit of U.S. Provisional Patent Application No. 61/979,298, filed Apr. 14, 2014, the disclosures of which are incorporated herein in their entirety.

STATEMENT REGARDING GOVERNMENT SPONSORED RESEARCH

This invention was made with government support under DE-SC0004993/T-105630 awarded by the U.S. Department of Energy. The government has certain rights in the invention.

FIELD OF THE INVENTION

The present invention relates to electrochemistry, and more particularly, to devices for performance of electrochemical experiments.

BACKGROUND

Techniques such as combinatorial chemistry have made it possible to generate large numbers of compounds that may be useful as electrocatalysts, photocatalysts, and/or photoabsorbers. It is often desirable to perform electrochemical experiments on these compounds in order to identify compounds having desirable characteristics. However, because of the large number of compounds being considered it is often desirable to perform these experiments using small amounts of the compound in combination with small amounts of electrolyte solution. The systems that have been developed to perform electrochemical experiments on small amounts of compound have encountered undesirably high levels of resistance between the working electrode and the reference electrode. Further, reaction products from the electrochemical experiments can contaminate the small volume of the electrolyte solution. Additionally, gaseous reaction products can form bubbles in the electrolyte solution. The systems are also challenged by an inability to optically access the compound when it is desirable to perform photoelectrochemical experiments and incompatibility with scanning across a large number of different samples. As a result, there is a need for an improved system for performing electrochemical experiments.

SUMMARY

A drop of electrolyte solution is suspended between an electrochemical experiment probe and a test sample. The drop is used to perform an electrochemical experiment on the test sample while flowing electrolyte solution into the drop and removing an output solution from the drop.

In another embodiment, a drop of electrolyte solution is suspended between an electrochemical experiment probe and a test sample. The drop has a volume less than 1 μL and is used to perform electrochemical experiment on the test sample.

A system for performing electrochemical experiments includes an electrochemical experiment probe positioned over a test sample with a drop of liquid electrolyte solution suspended between the electrochemical experiment probe and the test sample. The system also includes one or more drop conduits arranged so as to add electrolyte solution to the drop and one or more output conduits arranged to remove output solution from the drop. In some instances, the one or more drop conduits and/or the one or more output conduits are included in the probe.

The system can include electronics that control a rate at which electrolyte solution is added to the drop and also the rate at which output solution is removed from the drop. In some instances, the output solution is removed from the drop through one or more output conduits. The electronics can control the flowrate through the one or more output conduits such that the total volumetric flowrate through the one or more output conduits exceeds the volumetric flowrate of electrolyte solution into the drop.

In another embodiment, the system includes electronics that control a rate at which electrolyte solution is added to the drop and also the rate at which output solution is removed from the drop. Additionally, the electronics perform the one or more electrochemical experiments on the test sample. The electronics perform the one or more electrochemical experiments concurrently with adding the electrolyte to the drop and concurrently with removing output solution from the drop.

In one embodiment, the disclosure provides an integrated and compact electrochemical cell design, where an illumination source, spectrometer, integrating sphere, reference electrode, counter electrode, and reactant/product flow channels are combined with translation stages to form a scanning electrochemical-optical instrument (FIG. 3). The material under investigation is illuminated by a source including but not limited to: light emitting diode, broadband light source, or laser. The light is delivered to the sample by fiber optic or free space beam path. The integrating sphere collects the optical signal, which may also be performed with other optical measurement devices including, but not limited to, photodiodes and fiber optics. The material under investigation is suspended under the scanning drop sensor such that the optical collection device, placed under the material, is aligned with the scanning drop sensor to measure the optical signal of interest. The scanning drop sensor and optical collection device move together during rastering of the sample to provide the lateral scanning feature. The optical signal from the optical collection device may be measured using instruments including, but not limited to, spectrometers and photodiodes. The light source and spectrometer can be automated through a software interface such that the light source is cycled between on/off states and spectra are collected during desired times within this cycle. This can be accomplished while electrochemical measurements are made, thus accomplishing operando characterization of electrochemical materials.

BRIEF DESCRIPTION OF THE FIGURES

FIG. 2A is a topview of the holder.

FIG. 2B is a cross section of the holder shown in FIG. 2A taken along the line labeled B in FIG. 2A.

DESCRIPTION

Figure 1:
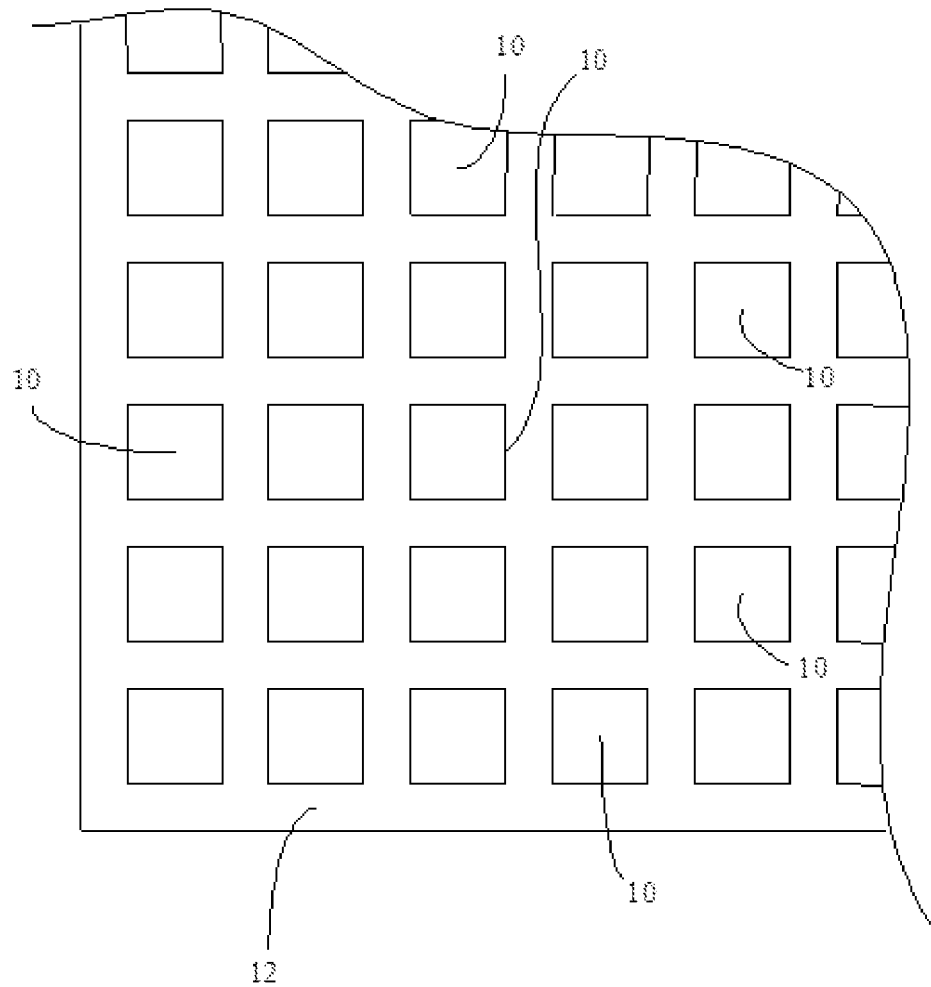
FIG. 1 is a topview of a portion of a sample array.

As used herein and in the appended claims, the singular forms "a," "and," and "the" include plural referents unless the context clearly dictates otherwise. Thus, for example, reference to "a device" includes a plurality of such devices and reference to "the drop cell" includes reference to one or more drop cells so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. However, with respect to any similar or identical terms found in both the incorporated publications or references and those expressly put forth or defined in this application, then those terms definitions or meanings expressly put forth in this application shall control in all respects. The publications discussed above and throughout the text are provided solely for their disclosure prior to the filing date of the present application. Nothing herein is to be construed as an admission that the inventors are not entitled to antedate such disclosure by virtue of prior disclosure.

A system for performing electrochemical experiments on multiple samples includes a probe positioned over an array of the samples. A drop of electrolyte solution is suspended between the probe and one of the samples that serves as a test sample. During the operation of the system electrolyte solution is added to the drop and output solution is removed from the drop. As a result, the contents of the drop are continuously replaced.

A working electrode is formed at interface between the drop and the test sample. A reference electrode can be positioned such that the functional portion of the reference electrode contacts the drop. The electrolyte solution is added to the drop by flowing the electrolyte solution or precursors for the electrolyte solution through one or more conduits included in the probe. A counter electrode can be positioned in one or more of these conduits. As a result, a liquid can concurrently contact the drop, the working electrode, and the functional portion of the reference electrode. Electronics that are in electrical communication with each of these electrodes can use these electrodes to perform electrochemical experiments such as cyclic voltammetry.

During the electrochemical experiments, reaction products can be generated at the counter electrode. The position of the counter electrode in the conduits allows reaction product at the counter electrode to be flushed from the system so they do not interfere with measurements at the working electrode. For instance, the system can be operated such that electrolyte solution or one or more precursors for the electrolyte solution flow over the counter electrode and then into the drop and out of the system. Alternately, when it is desirable to minimize or eliminate contact between the working electrode and reaction products generated at the counter electrode, the system can be operated such that the electrolyte solution or one or more precursors for the electrolyte solution flow over the counter electrode and then out of the system without contacting the working electrode.

In addition, the system provides the ability to include optical characterization of the material during electrochemical measurements. Such measurements can be time-resolved and synchronized with electrochemical experiments for applications including, but not limited to, optical transparency of materials, such as catalysts, whose transparency is a metric of performance in artificial photosynthesis; spectral transmission of materials, such as photoabsorbers and photocatalysts, to provide characterization of properties such as the optical bandgap; and spectral transmission measurements of unknown materials to elucidate their properties via basis-set reconstruction.

Practically any material can be modified by electrochemical measurements. For many applications, optical properties are relevant to the performance of the material and since the optical properties will in general be altered during an electrochemical experiment, real-time, in situ optical measurements are important for material characterization. One particular example is in the field of artificial photosynthesis. Many solar fuel generator designs involve illumination of a photoabsorber stack coated with a catalyst for the oxygen evolution reaction (OER). In this design, impinging light must pass through the catalyst layer before reaching the photoabsorbers, and thus transparency of the oxygen evolution catalyst is an important parameter. Intermediate phase changes that occur during OER may change transparency of the catalyst. Understanding when and how the transparency changes as OER occurs helps to optimize the components of the device and narrow down potential catalysts. Other examples lie in the fields of electrochromics and corrosion science.

The combined electrochemical-optical measurements may also be applied more generally even when optical characteristics are not pertinent to material performance. In this class of experiments, the optical measurement serves as an operando spectroscopy technique and functions as a materials characterization technique while the material is under an electrochemically-controlled environment.

The drop can have a sub-$\mu$L volume. For instance, in some instances, the drop has a volume less than 0.1 $\mu$L. The reduce volume of the drop combined with direct contact between the drop and both the working electrode and the reference electrode provides a low level of resistance between the working electrode and the reference electrode. Additional advantages are gained from the continuous replacement of the drop contents. For instance, reaction products at both the counter electrode and the working electrode enter the drop and are removed in the output solution. Similarly, any dissolution of a test sample into the drop is removed in the output solution. Likewise bubbles formed at the counter electrode and/or the working electrode during electrochemical experiments are removed in the output solution. As result, there is a reduced tendency for the electrolyte solution to become contaminated or for results to be affected by the presence of bubbles in the electrolyte solution, which could compromise electrolyte solution connectivity.

Additionally, the system is easily scanned from one sample to another because the probe itself need not contact the samples. For instance, the samples and the probe can be moved relative to one another while a substantially constant distance is maintained between the samples and the probe. This movement allows the probe to be scanned from one sample to the next. Since the distance between the probe and the sample does not substantially change, the drop is maintained between the probe and samples even when the probe and samples are being moved relative to one another. Further, refreshing of the drop can continue while the probe is scanned from one sample to the next. For instance, the drop can be refreshed at a rate of 1 to 10 times per second and the time to scan from one sample to another can be about 1 second. As a result, the drop volume has been refreshed at least once when scanning from one sample to another. Accordingly, the opportunity for cross contamination between different samples is reduced.

FIG. 1 is a topview of a portion of a sample collection. The sample collection includes multiple samples 10 arranged on a substrate 12. The samples 10 can each be a sample upon which one or more electrochemical experiments are to be performed. The samples 10 can be solids. Suitable samples include, but are not limited to, samples that include compounds generated from combinatorial chemistry. Suitable sample sizes include but are not limited to, sizes that occupy more than 500 $\mu m^2$ or 2500 $\mu m^2$ and/or less than 0.1 $mm^2$, 1 $mm^2$, or 10 $mm^2$ of the substrate 12. For instance, the samples can be square or substantially square and have sizes in a range of 50 $\mu m \times 50$ $\mu m$ to 3 mm×3 mm or more. Although the samples are shown as being spaced apart from one another, the samples can alternately exist as a continuous layer on top of the substrate. Continuous samples can have a spatial variation in a material property such as chemical composition.

The substrate 12 can be electrically conductive. Suitable substrates 12 include, but are not limited to, metals such as iron, titanium, and molybdenum. Although only a portion of the sample collection is shown, the sample collection can include hundreds or even thousands of samples 10.

Figure 2A:
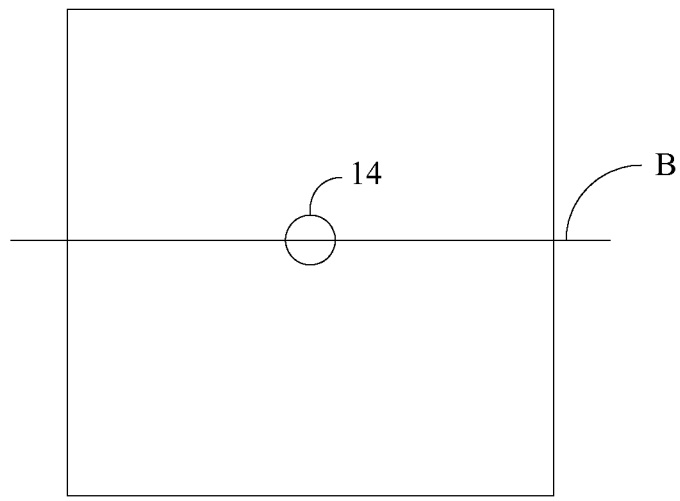
FIG. 2A and FIG. 2B illustrate a holder for a probe for performing electrochemical experiments on the samples of FIG. 1.
Figure 2B:
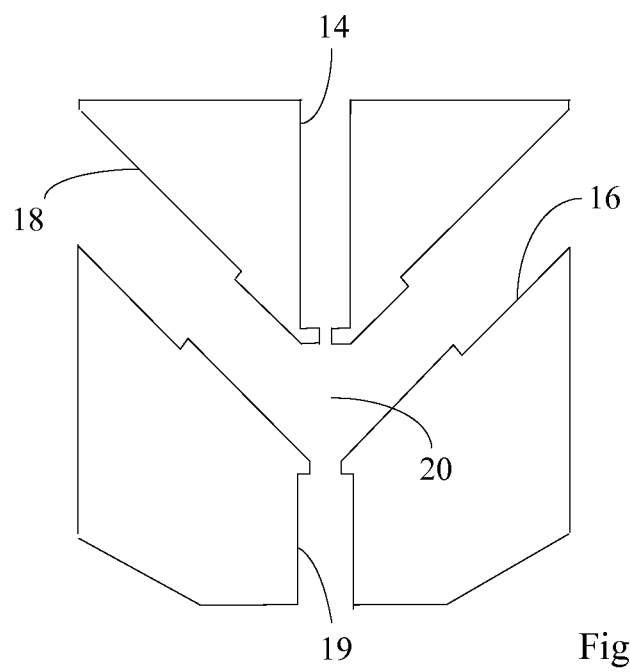

FIG. 2A and FIG. 2B illustrate a holder for a probe for performing electrochemical experiments on the samples 10 of FIG. 1. FIG. 2A is a topview of the holder and FIG. 2B is a cross section of the holder shown in FIG. 2A taken along the line labeled B in FIG. 2A. The holder defines an optical port 14, a first port 16, a second port 18, and a drop port 19. The first port 16, the second port 18, and the drop port 19 are each configured to receive a fluid conduit. The holder also defines an interconnect channel 20 configured to guide the flow of a fluid such as a liquid. The material for the holder can be electrically insulating. Examples of suitable materials for an electrically insulating holder include, but are not limited to, Poly(methyl methacrylate) (acrylic glass), polypropylene and Polytetrafluoroethylene (PTFE). The material for the holder can also be electrically conducting. In some instances, an electrically conducting holder can serve as a counter electrode in the electrochemical experiments discussed below. Examples of suitable materials for an electrically conducting holder include, but are not limited to, iron, copper and molybdenum, with and without coatings such as gold and platinum.

Figure 3:
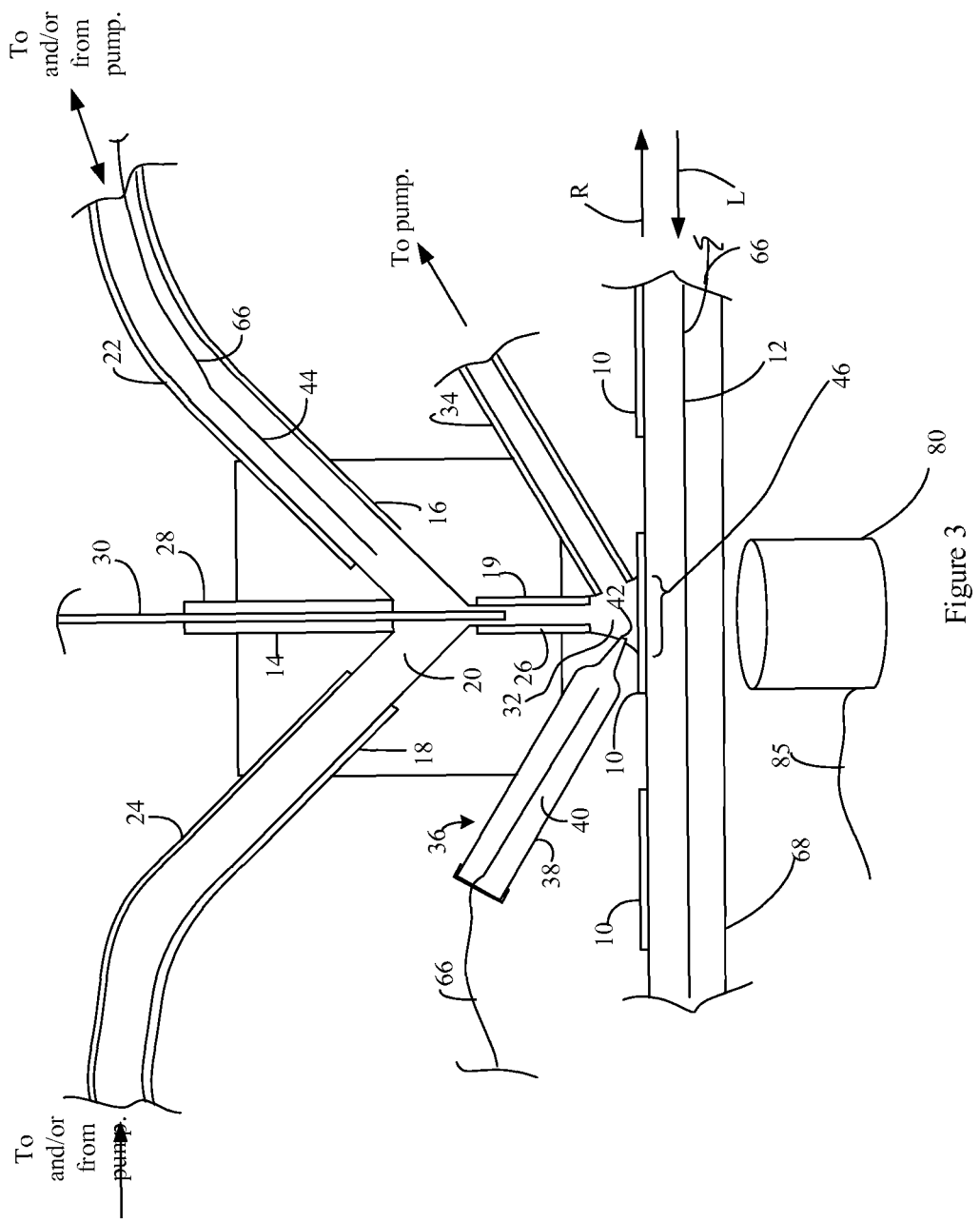
FIG. 3 illustrates a portion of a system for performing electrochemical experiments on a collection of samples.

FIG. 3 illustrates a system for performing electrochemical experiments on the samples 10 of FIG. 1. The system includes a probe positioned over a sample 10 that is included in a sample collection such as the sample collection of FIG. 1. The probe includes the holder illustrated in FIG. 2A and FIG. 2B. In particular, FIG. 3 shows the cross section of the holder as illustrated in FIG. 2B. Additionally, FIG. 3 shows a cross section of the collection of samples shown in FIG. 1.

A first conduit 22 is connected to the first port 16 such that a first precursor liquid flowing in the first conduit 22 is in fluid communication with the interconnect channel 20. A second conduit 24 is connected to the second port 18 such that a second precursor liquid flowing in the second conduit 24 is in fluid communication with the interconnect channel 20. As a result, the first precursor liquid and the second precursor liquid can interact and mix in the interconnect channel 20. A drop conduit 26 is connected to the drop port 19 such that the fluids in interconnect channel 20 are in fluid communication with a fluid in the drop conduit 26.

A waveguide holder 28 holds an optical waveguide 30 and is connected to the optical port 14 such that light that exits from the waveguide 30 is directed toward an exit of the drop conduit 26. Accordingly, when the drop conduit 26 is positioned over a sample 10 as shown in FIG. 3, the light exiting from the waveguide 30 exits from the drop conduit 26 and is incident upon the sample 10. FIG. 3 illustrates the waveguide 30 extending through the interconnect channel 20 and into the drop conduit 26. However, the waveguide 30 need not extend into either the drop conduit 26 and/or the interconnect channel 20. Suitable waveguides 30 include, but are not limited to, optical fibers.

A liquid drop 32 is suspended between the drop conduit 26 and the sample 10 collection without the drop conduit 26 contacting the sample 10. In some instances, no portion of the probe contacts the sample 10, the substrate, or the collection of samples. An output conduit 34 is positioned such that a first end of the output conduit 34 is adjacent to an exit of the drop conduit 26. In particular, the output conduit 34 is positioned such that the output conduit 34 can withdraw or remove liquid from the drop 32. As a result, FIG. 3 illustrates an end of the output conduit 34 positioned in contact with the drop 32 of, e.g., electrolyte solution. In some instances, the output conduit 34 is immobilized relative to the holder. Suitable approaches for immobilizing the output conduit 34 relative to the holder include, but are not limited to, gluing with epoxies, mechanically mounting and clamping with suitable machined parts.

The system also includes a reference electrode 36 having an operational end in contact with the drop 32. The reference electrode 36 can have a container 38 that defines a reservoir 40 that contains a solution. An operational end of the reference electrode 36 can include an opening that is in fluid communication with the reservoir 40. A suitable diameter for the opening includes diameters less than 100 $\mu m$.

A porous material 42 can be positioned across the opening in the container 38 such that the porous material 42 contacts both the drop 32 and a reference solution in the reservoir 40. Suitable porous materials include, but are not limited to, frits, asbestos membranes and polymer membranes. Suitable frits include, but are not limited to, glass frits, ceramic frits and composite frits.

Suitable reference electrodes 36 include, but are not limited to, capillary electrodes, tapered micrometer tubing and machined micrometer ports. Examples of suitable capillary electrodes include pulled capillary electrodes. One example of a suitable pulled capillary reference electrode 36 is an Ag/AgCl electrode that includes a silver wire immersed in a reference solution that includes silver chloride. In some instances, the reference electrode 36 is immobilized relative to the holder. Suitable approaches for immobilizing the output conduit 34 relative to the holder include, but are not limited to, gluing with epoxies, mechanically mounting and clamping with suitable machined parts.

Although FIG. 3 illustrates the reference electrode 36 as being capped, the solution in the reference electrode 36 can optionally be flowed through the reference electrode 36 as is discussed in more detail below.

The system also includes a counter electrode 44 (alternately called an auxiliary electrode). The counter electrode 44 need not be in direct contact with the drop 32. For instance, it is often sufficient for the electrolyte solution and/or one or more liquid precursor for the electrolyte solution to concurrently contact both the counter electrode 44 and the drop 32. As a result, the counter electrode 44 can be positioned in the interconnect channel 20 and/or one or more of the fluid conduits such as the drop conduit 26. FIG. 3 shows the counter electrode 44 positioned in the interconnect channel 20 and the first conduit 22. As an alternative to the counter electrode being positioned in the interconnect channel 20 and/or one or more of the fluid conduits such as the drop conduit 26, an electrically conducting holder can serve as the counter electrode.

The system also includes a working electrode 46 defined by the location where the sample collection contacts the drop 32. In some instances, the drop volume is controlled to provide a working electrode 46 that is greater than more than 100 $\mu m^2$, 500 $\mu m^2$ or 2500 $\mu m^2$ and/or less than 0.1 $mm^2$, 1 $mm^2$, or 10 $mm^2$ of the substrate 12. These reduced sizes permit the use of smaller sample sizes with sample length scale varying from 30 $\mu m$ to 3 mm.

Although FIG. 3 illustrates the probe configured such that the drop conduit 26 and the holder are separate components, the drop conduit 26 can be integrated into the holder. Suitable conduits for the first conduit 22, the second conduit 24, and the drop conduit 26 include, but are not limited to, capillaries, capillary-scale tubing, and mm-scale tubing. Although FIG. 3 illustrates the conduits as being a single piece, the conduits can be assembled from multiple pieces. For instance, one or more conduits selected from the first conduit, the second conduit, and the drop conduit can include a connector and a tube such as a capillary or mm-scale tubing. The connector can act as an interface between the holder and the tube. For instance, the connector can be designed to be inserted into a port so a seal is formed between the connector and the holder. Additionally or alternately, the tube can be slid onto the connector so a seal is formed between the tube and the connector.

FIG. 3 also depicts a substrate 12. As described below, the substrate can be electrically conductive. In some embodiments, the substrate can allow light to pass through the substrate 12. In a further embodiment, an optional stage 68 is present. The stage can support the substrate 12. In some embodiments, the stage is substantially transparent. Also depicted is an optional optical collection device 80. The optical collection device 80 can be used to monitor changes in color, opacity, fluorescence and luminescence of sample 10. A fiber optic cable 85 optically links the optical collection device 80 to a spectrometer or other light sensing device (not shown). The optical collection device 80 can be an integrating sphere (Ulbricht sphere). In another embodiment, the optical collection device 80 can be an optical sensing array (e.g., a CCD camera).

Figure 4:
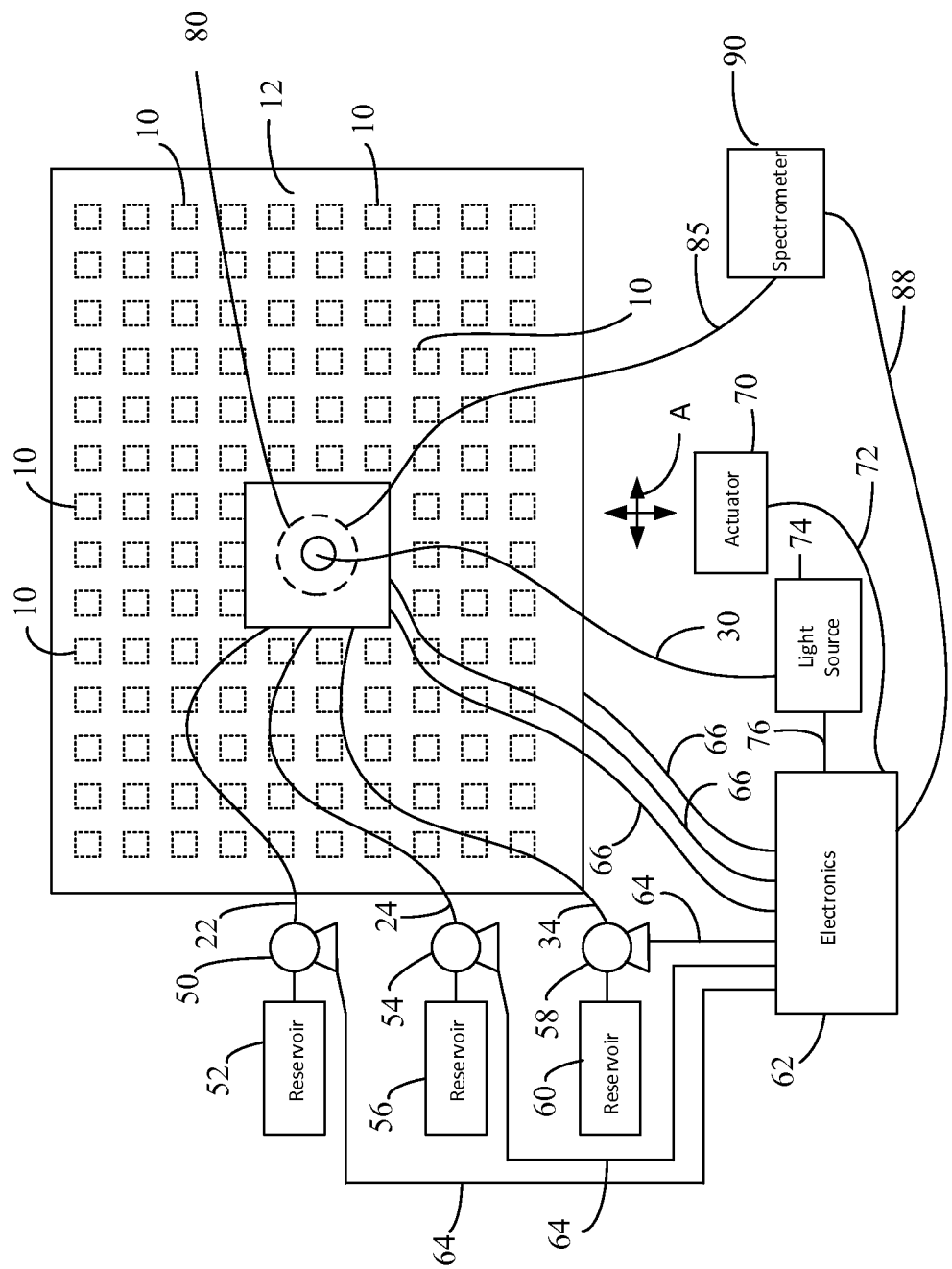
FIG. 4 is a schematic diagram illustrating operation of the system of FIG. 3.

FIG. 4 is a schematic diagram illustrating operation of the system of FIG. 3. Several fluid conduits each provides fluid communication between the holder and a reservoir. The system also includes several pumps that are each positioned along one of the fluid conduits such that the pump controls the flow of fluid through the fluid conduit. For instance, a different pump (50, 54 and 58) is positioned along the first conduit 22, the second conduit 24, and the output conduit 34.

The pumps control the flow of fluids between the holder and one of the reservoirs (e.g., 52, 56 and 60). For instance, a first pump 50 positioned along the first conduit 22 controls the flow of a first precursor liquid from a first precursor reservoir 52 through the first conduit 22 and into the interconnect channel 20 within the holder. A second pump 54 positioned along the second conduit 24 controls the flow of a second precursor liquid from a second precursor reservoir 56 through the second conduit 24 and into the interconnect channel 20 within the holder. A third pump 58 positioned along the output conduit 34 controls the flow of output solution from the drop 32 through the output conduit 34 and into an output solution reservoir 60. Suitable pumps include, but are not limited to, peristaltic pumps, syringe pumps, microfluidic pumps, and gravity feeds. The system includes electronics 62 for controlling the performance of the electrochemical experiments. Pump conductors 64 provide electrical communication between each of the pumps and the electronics 62 and permit the electronics 62 to operate each of the pumps. For instance, the electronics 62 can operate the pumps so as to control the flow rate and/or directions of a fluid in the associated conduit.

The system also includes electrode conductors 66 that are each in electrical communication with a different one of the electrodes. For instance, one of the electrode conductors 66 is in electrical communication with the reference electrode and another of the reference electrodes is in electrical communication with the counter electrode. The electrode conductor that is in electrical communication with the working electrode need only be in electrical communication with the substrate 12. For instance, the electrode conductor need only be electrically connected to the substrate 12 as is illustrated. As noted above, the substrate 12 can be electrically conducting. Since the portion of the sample collection contacted by the drop 32 serves as the working electrode 46, the electrically conducting substrate 12 provides an electrical connection between the electrode conductor and the working electrode 46.

The system also includes one or more actuators 70 that are configured to move the sample collection and the holder relative to one another. For instance, the one or more actuators 70 can be configured to move the sample collection while the holder is stationary or to move the holder while the sample collection is stationary. Alternately, the one or more actuators 70 can be configured to move the sample collection and the holder. In one example, the one or more actuators 70 are configured to move the sample collection while the holder is stationary and the movement is in a substantially two-dimensional plane illustrated by the arrows labeled A. Movement of the sample collection in this two-dimensional plane is such that the distance between the sample collection and the holder is not substantially changed as a result of the movement. Accordingly, the movement of the sample collection can change the sample 10 over which the holder is positioned. Actuator conductors 72 provide electrical communication between the electronics 62 and the one or more actuators 70 such that the electronics 62 can control movement of the sample collection and the holder relative to one another. Suitable actuators 70 include, but are not limited to, motorized precision linear stages and manual positioners. In some embodiments, the actuator 70 comprises a motorized stage similar to a microscope stage that can be moved in the X-Y and optionally Z directions.

The system also includes a light source 74. The light source 74 is optically coupled with the waveguide 30 such that the light source 74 functions as the source of the light output by the waveguide 30. Light source conductors 76 provide electrical communication between the light source 74 and the electronics 62 such that the electronics 62 can control operation of the light source 74. For instance, the electronics 62 can control the power and/or intensity of the light output by the light source 74. Accordingly, the electronics 62 can control the power and/or intensity of the light that is incident upon the sample 10 before, after, and/or during an electrochemical experiment. The light source can be monochromatic or polychromatic. Suitable light sources include, but are not limited to, lasers, light-emitting diodes, Xenon arc lamps, and solar stimulators.

The system can optionally include an optical collection device 80 positioned below the sample 10 and the light source 74. The optical collection device 80 can comprise an integrating sphere, an optical sensing array such as a CCD camera or the like. The optical collection device 80 can be linked to a spectrometer 90 by an optical fiber 85. The CCD or spectrometer measures changes in light intensity, color or hue. The spectrometer 90 or optical array are connected by conductors 88 to provide electrical communication between the electronics 62 and the spectrometer 90 or optical array such that the electronics 62 can control collection of optical data from the sample.

Suitable electronics 62 for operating the above system can include one or more controllers. A suitable controller includes, but is not limited to, a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions attributed to the electronics 62. A general-purpose processor may be a microprocessor, but in the alternative, the controller may include or consist of any conventional processor, microcontroller, or state machine. A controller may also be implemented as a combination of computing devices, e.g., a combination of a DSP and a microprocessor, a plurality of microprocessors, one or more microprocessors in conjunction with a DSP core, or any other such configuration. The electronics 62 can optionally include one or more memories in communication with the controller. The electronics 62 can store data for executing the functions of the electronics 62 in the memory. The memory can be any memory device or combination of memory devices suitable for read and/or write operations. In some instances, the electronics 62 include one or more computer-readable media in communication with the controller. A suitable computer-readable medium can have a set of instructions to be executed by the controller. The controller can read and execute instructions included on the computer-readable medium. The controller executes the instructions such that the electronics 62 perform one or more of the described functions. The computer-readable medium cab be different from the memory or can be the same as the memory. Suitable computer-readable media include, but are not limited to, optical discs such as CDs, magnetic storage diskettes, Zip disks, magnetic tapes, hard drives, RAMs, and ROMs. Some functions of the electronics 62 may be executed using hardware as opposed to executing these functions in firmware and/or software.

Before operating the system, a first precursor liquid can be placed in the first precursor reservoir 52 and/or a second precursor liquid can be placed in the second precursor reservoir 56. During operation of the system, the electronics 62 operate the first pump 50 and/or the second pump 54 such that the first precursor liquid and/or the second precursor liquid flow into the interconnect channel 20 where the result operates as the desired electrolyte solution. When the first precursor liquid and the second precursor liquid flow into the interconnect channel 20, the first precursor liquid and the second precursor liquid can mix to become the electrolyte solution. The electrolyte solution flows out of the interconnect channel 20, through the drop conduit 26 and into the drop 32. When only the first precursor liquid flows into the interconnect channel 20, the first precursor liquid serves as the electrolyte solution. As noted above, it may be desirable for reaction products at the counter electrode 44 to be removed from the electrolyte solution and/or the drop 32. As a result, when all or a portion of the counter electrode 44 is positioned in the first conduit 22 it may be desirable for the first precursor liquid to be included in the electrolyte solution in order to maintain a flow of the first precursor liquid over the counter electrode 44 and into the drop 32.

The electronics can form the drop by operating the pumps in patterns other than the pattern disclosed above. For instance, before operating the system, a second precursor liquid can be placed in the second precursor reservoir 56. During operation of the system, the electronics 62 operate the second pump such that the second precursor liquid flows into the interconnect channel 20 where the result operates as the desired electrolyte solution. Rather than operating the first pump such that a first precursor liquid flows into the interconnect channel 20, the electronics can operate the first pump 50 such that the second precursor liquid flows out of the interconnect channel 20, through the first conduit 22, and into the first precursor reservoir 52. The electronics also operate the first pump 50 and second pump 54 so as to provide a flow rate of the electrolyte solution through the interconnect channel 20 that is sufficient for the electrolyte solution to exit from the interconnect channel 20 through the drop conduit 26 and into the drop 32. In this instance, the electrolyte solution flows over the counter electrode and then exits the holder through the first conduit 22 without contacting the working electrode. As a result, operating the pumps in this pattern is suitable for instances where it is not desirable for reaction products at the counter electrode to come into contact with the working electrode although the pumps can be operated in this pattern under other circumstances.

While operating the pumps such that the electrolyte solution flows out of the interconnect channel 20, through the drop conduit 26 and into the drop 32, the electronics 62 can form the drop by concurrently operating the third pump 58 such that the output conduit 34 removes a portion of the drop 32 as an output solution. The electronics 62 operate the pumps such the volumetric flow rate through the output conduit 34 exceeds the volumetric flowrate through the drop conduit 26. In order for the drop 32 to retain a substantially constant volume under these conditions, a portion of the atmosphere in which the drop 32 is positioned must also be pulled into the output conduit 34 along with the output solution.

The drop volume and/or shape can be controlled tuned by changing a flow ratio (volumetric flow rate through the output conduit 34:volumetric flowrate through the drop conduit 26). A suitable flow ratio is greater than 1:1, 2:1, or 4:1 and/or less than 7:1, 10:1, or 50:1. Suitable volumes for the drop 32 include, but are not limited to, volumes greater than 0.05 µL, or 0.1 µL, and/or less than 5 µL, 10 µL, or 50 µL.

The electronics 62 operate the one or more actuators 70 so the drop 32 is positioned on one of the samples. While the drop 32 is positioned on the sample, the electronics 62 apply electrical energy to the electrodes as needed to perform one or more electrochemical experiments on the sample. In addition, or optionally, spectrophotometric measurements can be made using the optical collection device 80. While one or more of the one or more electrochemical experiments or optical measurements is being performed, the electronics operate the pumps such that the electrolyte solution is being added to the drop and the output solution is being removed from the drop. Further, the electronics 62 can continue to operate the pumps such the volumetric flow rate through the output conduit 34 exceeds the volumetric flowrate through the drop conduit 26. Examples of suitable electrochemical experiments include, but are not limited to, cyclic voltammetry, chronoamperometry, chronopotentiometry and electrochemical impedance spectroscopy. Another type of electrochemical experiment that can be formed includes photoelectrochemical experiments. The electronics 62 can operate the light source in conjunction with the application of electrical energy to the electrodes as needed to perform one or more photoelectrochemical experiments on the sample. Examples of suitable photoelectrochemical experiments include, but are not limited to, light-modulated cyclic voltammetry, illuminated open-circuit voltage measurements, short-circuit photocurrent measurements, light-biased impedance measurements, and detection of luminescence, fluorescence, opacity and the like.

After performing the one or more electrochemical experiments and/or optical experiments upon a sample, the electronics 62 can operate the one or more actuators 70 so the drop 32 of electrolyte solution is positioned over a second one of the samples so one or more electrochemical and/or optical experiments can be performed on the second sample. During the movement of the probe from sample to sample, the electronics 62 continue to operate the pumps so the drop 32 is present between the output conduit 34 and the sample collection. Additionally, during the movement of the probe from sample to sample, the electronics operate the pumps such that the electrolyte solution is being added to the drop and the output solution is being removed from the drop. Further, the electronics 62 can continue to operate the pumps such the volumetric flow rate through the output conduit 34 exceeds the volumetric flowrate through the drop conduit 26. The process of moving from sample to sample and performing one or more electrochemical experiments permits all or a portion of the samples to be quickly scanned and tested.

Although the above system is disclosed as having a single output conduit 34, it may be desirable to have multiple output conduits 34. The location of an output conduit 34 can affect the desired scanning direction. For instance, the arrows labeled R and L in FIG. 3 illustrates that the sample collection can be moved either left or right relative to the holder. When the sample collection is moved to the left relative to a stationary holder as is shown by the arrow labeled L, the movement pulls the drop 32 away from the output conduit 34. As a result, droplets of the electrolyte solution can break away from the drop 32 and remain on the sample collection. However, when moving the sample collection in the opposite direction, the drop 32 moves toward the output conduit 34. Since the output conduit 34 is withdrawing electrolyte solution from the drop 32, the tendency of droplets to break way from the larger drop 32 is reduced. Accordingly, it can be more desirable to move the sample collection and/or holder such that the drop 32 moves toward the output conduit 34. However, as is evident from FIG. 1, the samples can be arranged in two dimensions. Accordingly, it may be desirable to add more than one output conduit 34. For instance, the system can include another output conduit 34 arranged as shown in FIG. 3 but with the output conduit 34 extending into the page and/or another output conduit 34 arranged as shown in FIG. 3 but with the output conduit 34 extending into the page. The total volumetric output flowrate is the total of the volumetric flowrates through all output conduits 34. The electronics 62 operate the system so the total volumetric output flowrate satisfies the conditions discussed above. For instance, the electronics 62 operate the pumps such the total volumetric output flowrate exceeds the volumetric flowrate through the drop conduit 26. A suitable ratio for the total volumetric output flowrate:total volumetric flowrate through the one or more drop conduits 26 that each adds electrolyte solution to the drop is greater than 1:1, 2:1, or 4:1 and/or less than 7:1, 10:1, or 50:1.

Although FIG. 3 illustrates the reference electrode as being capped, the solution in the reference electrode can optionally be flowed through the reference electrode. For instance, the electronics 62 can control a pump for pumping reference electrode solution into the reservoir of the reference electrode. The displaced solution in the reservoir can flow out the porous material across the opening of the reference electrode. This arrangement may be desirable in order to prevent the reference electrode solution from becoming contaminated by liquid from the drop 32. The reference electrode solution that flows through the porous material can flow into the drop and then exit the drop in the output solution.

Although FIG. 3 and FIG. 4 illustrate the holder as including multiple a first port and a second port, the holder can include a single port. For instance, the holder can include the first port 16 and exclude the second port 18. Additionally or alternately, the holder can include more ports than the first port and the second port. The introduction of additional ports permits the use of additional precursor liquids and accordingly presents a broader possible range of electrolyte solutions.

Alternative arrangements are possible for the components of the holder. For instance, the reference electrode can be positioned in the optical port 14 such that the functional end of the reference electrode is in the drop. With this arrangement, the reference electrode illustrated in FIG. 3 need not be replaced with another component or could be replaced with one or more components such as an optical waveguide that can be operated as the waveguide disclosed above, or an output conduit 34 that can be operated as the output conduits 34 disclosed above.

The substrate 66 and/or stage 68 should be substantially optically transparent when used in conjunction with an optical collection device 80, when the optical collection device 80 is configured below the sample as depicted in FIG. 3. However, it should be noted that the optical detection device can be configured elsewhere in the system (e.g., above or at an angle above the sample). The optical collection device 80 is used to obtain transmitted, reflected or emitted light from the sample prior to, during and/or after electrochemical measurements. For example, many solar fuel generator designs involve illumination of a photoabsorber stack coated with a catalyst for the oxygen evolution reaction (OER). In this design, impinging light must pass through the catalyst layer before reaching the photoabsorbers, and thus transparency of the oxygen evolution catalyst is an important parameter. Intermediate phase changes that occur during OER may change transparency of the catalyst. Understanding when and how the transparency changes as OER occurs helps to optimize the components of the device and narrow down potential catalysts. The optical collection device allows for such measurements during electrochemical experiments.

EXAMPLE

The above system was employed to measure the electrochemical and photoelectrochemical performance of (photo) catalysts for oxygen evolution reactions. 1 M sodium hydroxide that was saturated with oxygen was used as the electrolyte solution. The volumetric flowrate into the holder through the second conduit 24 was 1 µL/s, out of the holder through the first conduit 22 was 0.2 µL/s. This yielded a flowrate of 0.8 µL/s out of the holder through drop conduit 26. The flow rate away from the drop through the output conduit 34 was fixed at 1.6 µL/s so that on average conduit 34 carried 0.8 µL/s of electrolyte solution and 0.8 µL/s of ambient atmosphere. An optical fiber coupled with an LED light source with an output power of 0.5 mW at 385 nm was employed as the illumination source. Various (photo) electrochemical measurements were performed on a quasi-quaternary metal oxide library, $NiFeCoTiO_x$, including cyclic voltammetry (CV), chopped illumination CVs, open-circuit potential measurements, chronoamperometry and chronopotentiometry with or without chopped illuminations. The sensitivity of the cell to sub-10 µA $cm^{-2}$ photocurrent was demonstrated in a chronoamperometric experiment with chopped illumination, and the high throughput operation of the cell was demonstrated by performing a 0.6 V, full-cycle CV at a throughput of one sample every 4 s.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

The invention claimed is:

1. A system, comprising:
  an electrochemical experiment probe configured to be positioned over a test sample with a drop of liquid electrolyte solution suspended between the electrochemical experiment probe and the test sample;
  one or more first conduits arranged so as to add electrolyte solution to the drop; and
  one or more output conduits arranged to remove output solution from the test sample, and
  a drop conduit in fluid communication with the one or more first conduits and comprising a drop port open to the test sample,
  wherein the one or more output conduits are positioned such that a first end of an output conduit is adjacent to an exit of the drop conduit, and
  an optical collection device placed under the test sample, a fiber optic cable optically linking the optical collection device to a spectrometer,
  wherein the optical collection device is aligned with the scanning drop sensor and the scanning drop sensor and optical collection device move together during rastering of the sample.

2. The system of claim 1, wherein the one or more first conduits are included in the probe.

3. The system of claim 2, wherein the test sample is one of a plurality of samples and further comprising:
  a sample collection including the samples positioned on an electrically conducting substrate.

4. The system of claim 2, further comprising:
  electronics configured to control a flow of electrolyte solution through the one or more first conduits such that the electrolyte solution is added to the drop and to control a flow of an output solution through the one or more output conduits such that the output solution is removed from the drop and flows through the one or more output conduits.

5. The system of claim 4, wherein the one or more output conduits each contacts the drop.

6. The system of claim 5, wherein the electronics control a volumetric flowrate through the one or more output conduits such that the volumetric flowrate through the one or more output conduits exceeds the volumetric flowrate of electrolyte solution into the drop.

7. The system of claim 5, wherein the electronics control the flow of output solution out of the drop through the one or more output conduits such that both the output solution and an atmosphere in which the drop is positioned flow through the one or more output conduits.

8. The system of claim 4, further comprising:
  a reference electrode having a functional end in physical contact with the drop.

9. The system of claim 4, further comprising: a counter electrode is positioned in one or more of the first conduits such that a liquid is in contact with both the drop and the counter electrode.

10. The system of claim 4, further comprising:
  wherein the electronics are configured to perform one or more electrochemical experiments on the test sample.

11. The system of claim 10, wherein the one or more electrochemical experiments make use of a working electrode, a counter electrode, and a reference electrode; and
  the reference electrode has a functional end in physical contact with the drop;
  the counter electrode is positioned in one or more of the first conduits such that a liquid is in contact with both the drop and the counter electrode; and
  the working electrode is defined by a location where the drop contacts the test sample.

12. The system of claim 10, wherein the electronics perform the one or more electrochemical experiments on the test sample concurrently with adding the electrolyte to the drop and concurrently with removing output solution from the drop.

13. The system of claim 11, wherein the drop has a volume less than 1 µL.

14. The system of claim 12, wherein the test sample occupies an area of the substrate less than 1 $mm^2$.

15. The system of claim 4, further comprising:
  one or more actuators configured to move the sample collection and the probe relative to one another.

16. The system of claim 1, further comprising:
  an optical waveguide positioned such that light exiting from the waveguide travels to the drop through one or more of the first conduits.

17. The system of claim 1, further comprising:
  a waveguide positioned in one or more of the first conduits such that light that exits from the waveguide travels through the drop to the test sample.

* * * * *